United States Patent
Pothula

(10) Patent No.: US 6,383,194 B1
(45) Date of Patent: May 7, 2002

(54) FLEXIBLE ULTRASONIC SURGICAL SNARE

(76) Inventor: Viswanadham Pothula, Box 10015, Camp Lejeune, NC (US) 28547

( * ) Notice: Subject to any disclaimer, the term of this patent is extended or adjusted under 35 U.S.C. 154(b) by 0 days.

(21) Appl. No.: 09/792,161

(22) Filed: Feb. 26, 2001

(51) Int. Cl.[7] .............................................. A61B 17/32
(52) U.S. Cl. ........................... 606/113; 606/46; 600/22
(58) Field of Search ................................ 606/113, 110, 606/114, 46, 128, 131, 167; 604/22

(56) References Cited

U.S. PATENT DOCUMENTS

| | | | | |
|---|---|---|---|---|
| 736,744 A | * | 8/1903 | Kratzmueller | 606/113 |
| 974,879 A | * | 11/1910 | Gwinn | 606/113 |
| 5,158,561 A | * | 10/1992 | Rydell et al. | 606/113 |
| 5,626,593 A | | 5/1997 | Imram | |
| 5,897,523 A | | 4/1999 | Wright | |
| 5,971,994 A | * | 10/1999 | Fritzsch | 606/113 |
| 5,989,264 A | * | 11/1999 | Wright | 606/113 |
| 6,231,578 B1 | * | 5/2001 | Rajhansa | 606/113 |

* cited by examiner

Primary Examiner—Pedro Philogene
(74) Attorney, Agent, or Firm—Alvin S. Blum

(57) ABSTRACT

An ultrasonically vibrating snare wire at the end of an elongate flexible waveguide can fit through an endoscope inserted in a patient's intestine. The wire loop can be extended past the distal end of the endoscope to grasp a polyp projecting from the intestinal wall. While the wire is vibrating at ultrasonic frequency, the loop is closed. This cuts and coagulates the tissue to stop bleeding. The ultrasonic cutting is more localized than electrocautery for more precise excision.

3 Claims, 2 Drawing Sheets

FLEXIBLE ULTRASONIC SURGICAL SNARE

FIELD OF THE INVENTION

This invention relates to apparatus for surgical excision of tissue, and more particularly to such apparatus that employs a snare wire energized with ultrasound to grasp, cut, and coagulate the tissue.

BACKGROUND OF THE INVENTION

In the practice of surgery, it is well known to employ a wire loop, or snare, to encircle a tissue to be cut. The wire is energized with electricity that enables the tissue to be coagulated as it is being cut. This stops the bleeding. The procedure is commonly applied for surgical excision of the tonsils. It is also employed through an endoscope to remove polyps from the intestine. In this case the snare assembly must be very long, greater than 150 centimeters. A problem encountered with this technique is that the coagulation or electrocautery action is not very localized. It occasionally happens that the adjacent intestinal tissue is injured enough to cause perforation of the intestinal wall with serious consequences. In many surgical applications, electrocautery is being replaced by ultrasound cutting and cauterizing. In this case a sharp rigid blade is vibrated at ultrasound frequencies and applied to a surface to be cut. The blade vibrates the tissue surface, cutting and coagulating the tissue as it advances to prevent bleeding. Because the action is localized to the tissue directly in contact with the blade, there is no spread of damage to adjacent tissue.

U.S. Pat. No. 5,989,264 issued Nov. 23, 1999 to Wright discloses an ultrasonic polyp snare designed to grasp, cut and coagulate polyps in the intestine through a flexible endoscope. A rigid blade at the distal end of an elongate flexible waveguide is excited by an ultrasonic transducer at the proximal end of the waveguide. A snare wire affixed to the distal end of the blade extends past the blade and along the waveguide to its proximal end. The blade and wire are maneuvered to surround the polyp at its base. This may be difficult when the polyp has a mushroom shape, because the blade is rigid. The snare wire must then be greatly enlarged to fit over the large polyp head. The apparatus may not be easily passed through the tortuous path that the endoscope may follow in certain intestines, because the blade is rigid. Surgeons developed great skill in manipulating a snare wire at the end of the catheter. The manipulation required by the Wright device with the snare on the side of the blade would require further training. It will not be as easily mastered.

SUMMARY OF THE INVENTION

It is accordingly an object of the invention to provide an ultrasonically vibrating snare wire at the end of an elongate flexible waveguide that can grasp, cut, and coagulate tissue. It is another object that the snare be operable at the end of an endoscope that is inserted into the intestines. It is yet another object that the snare be operable in a manner similar to an electrocautery snare to facilitate operator usage. The flexible ultrasonic surgical snare of the invention comprises an elongate flexible tubular sheath. A flexible waveguide having proximal and distal ends extends through the sheath. Ultrasonic vibrations are applied to the proximal end of the waveguide. The distal end of the waveguide is ultrasonically coupled to a wire loop or snare. The snare can be extended beyond the sheath to encircle a polyp, and then retracted into the sheath by operation of the proximal ends of the sheath and/or waveguide while the snare is vibrated at ultrasonic frequency to cut and coagulate the polyp. In operation, an endoscope is passed into the intestine. When polyps are found, the snare is passed through the endoscope and the snare extended to encircle the polyp. With the snare vibrating, the snare is retracted into the sheath to cut off and coagulate the polyp. In a first embodiment of the invention, both legs of the loop are affixed to the distal end of the waveguide, and the loop is retracted by retraction of the waveguide relative to the sheath. In a second embodiment of the invention, one leg of the loop is affixed to the distal end of the waveguide, and the second leg of the loop extends in an elongate wire back to the proximal end of the sheath, and the loop is retracted by pulling on the proximal end of the extended leg.

These and other objects, features, and advantages of the invention will become more apparent when the detailed description is studied in conjunction with the drawings in which like elements are designated by like reference characters in the various drawing figures.

DETAILED DESCRIPTION OF PREFERRED EMBODIMENTS

Figure 1:
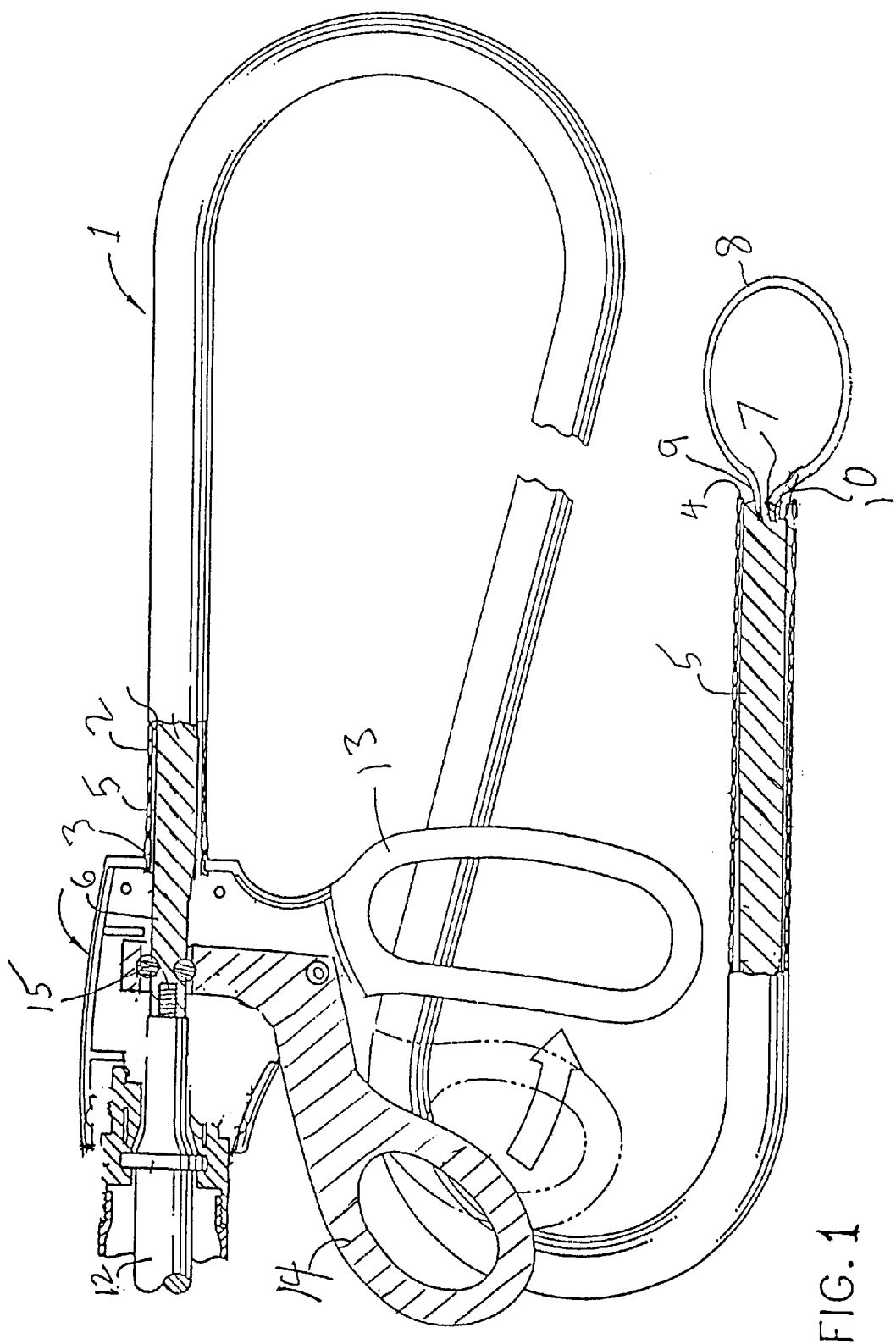
FIG. 1 is a perspective view of the surgical snare of the invention, partially broken away.

Referring now to drawing FIG. 1, an elongate, flexible surgical snare 1 of the invention is shown. It is preferably longer than 150 centimeters and sufficiently flexible to enable it to be inserted into an endoscope that may follow a tortuous path in the intestine of a patient and have the distal end extend just past the distal end of the endoscope. A flexible sheath 2 of a lubricous plastic covers a flexible waveguide 5. Extending from the distal end 4 of the sheath is a wire loop or snare 8 formed of a wire having a smaller diameter than the waveguide. Both legs 9, 10 of the loop are affixed to the distal end 7 of the waveguide by means such as welding or swaging that will enable effective transmission of ultrasonic vibration through the joint. The loop is extended from the sheath to encircle a polyp. The spring nature of the wire causes the loop to form. The proximal end 6 of the waveguide is coupled to an ultrasonic transducer or vibration element 12 to thereby transmit vibration to the wire snare to cut and coagulate tissue. The transducer and electric power to the transducer are conventional, and need not be further described. The proximal end 3 of the sheath is affixed to the handle 13. The proximal end 6 of the waveguide is connected to movable pivoted handle element 14 by resilient O-ring 15. The resilient nature prevents vibration from leaving the waveguide. The lubricous sheath material also retains the ultrasonic energy within the waveguide. While ultrasonic vibration is being applied to the wire, as the handle element 14 is brought to the closed position shown in phantom, the snare is retracted into the distal end of the sheath, closing the loop, and cutting and coagulating any tissue within the snare.

Figure 2:
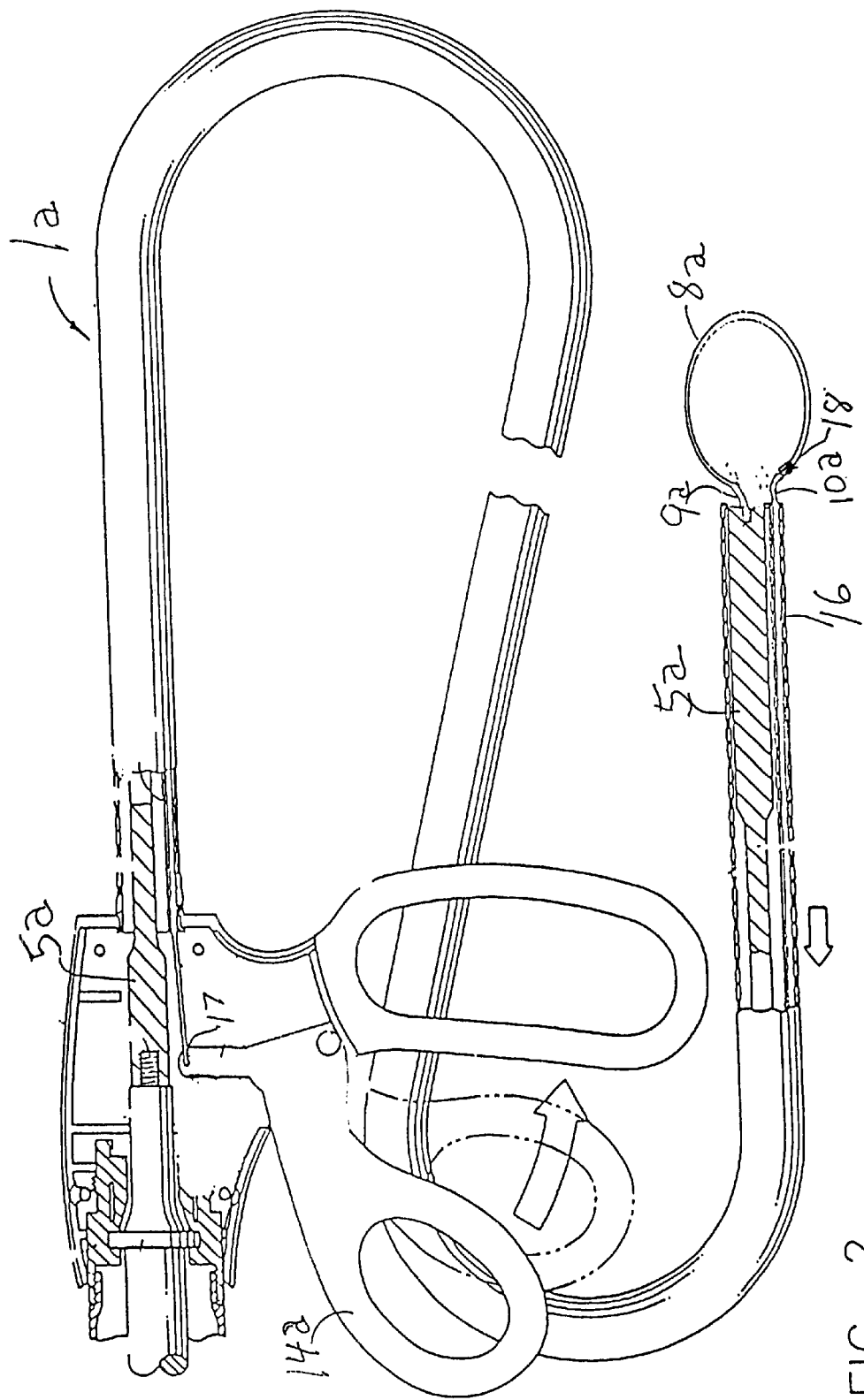
FIG. 2 is a perspective view of another embodiment of the surgical snare of the invention, partially broken away.

Referring now to the snare 1a shown in FIG. 2, the wire loop 8a has a first leg 9a affixed to the distal end of the waveguide 5a and a second leg 10a of the loop extending all the way to the handle through a separate tube 16. The proximal end 17 of wire leg 10a is coupled to the movable handle element 14a. as element 14a is moved toward the position shown in phantom, the leg 10a is pulled and the wire loop closes. The leg 10a may be provided with a resilient coupling 18 to retain the vibration within the loop.

While I have shown and described the preferred embodiments of my invention, it will be understood that the invention may be embodied otherwise than as herein specifically illustrated or described, and that certain changes in form and arrangement of parts and the specific manner of practicing the invention may be made within the underlying idea or principles of the invention.

What is claimed is:

1. A flexible ultrasonic surgical snare system comprising:
   a) a housing;
   b) an ultrasonic transducer affixed to the housing;
   c) an elongate flexible sheath having a proximal end attached to the housing, and a distal end;
   d) an elongate flexible ultrasonic waveguide passing through the sheath, the waveguide having a proximal end attached to the ultrasonic transducer for vibrating the waveguide, and a distal end;
   e) a wire having a proximal end and a distal end, the proximal end affixed to the distal end of the waveguide for transmission of ultrasonic vibrations to the wire;
   f) a loop in the wire intermediate the proximal and distal ends of the wire; and
   g) loop controlling means at the housing attached to the distal end of the wire for enlarging the loop to grasp tissue and for closing the loop to thereby cut, and coagulate the tissue by moving the distal end of the wire relative to the proximal end of the wire.

2. A flexible ultrasonic surgical snare assembly for grasping, cutting, and coagulating tissues, the snare assembly comprising:
   a) an ultrasonic vibration generator;
   b) an elongate flexible sheath having a proximal end and a distal end;
   c) an elongate flexible waveguide passing through the sheath, the waveguide having a proximal end coupled to the generator for transmission of vibrations thereto, and a distal end;
   d) a wire having a first end and a second end, the first end coupled to the distal end of the waveguide for transmission of ultrasonic vibrations to the wire;
   e) a loop in the wire intermediate the first and second ends; and
   f) loop controlling means operable from the proximal end of the sheath for enlarging the loop to grasp tissue and for closing the loop to thereby cut, and coagulate the tissue, in which the loop controlling means opens and closes the loop by moving the second end of the wire relative to the proximal end of the wire.

3. A flexible ultrasonic surgical snare assembly for grasping cutting and coagulating tissues, the snare assembly comprising:
   a) an ultrasonic vibration generator;
   b) an elongate flexible sheath having a proximal end and a distal end,;
   c) an elongate flexible waveguide passing through the sheath, the waveguide having a proximal end coupled to the generator for transmission of vibrations thereto, and a distal end;
   d) a wire having two legs with one of the legs coupled to the distal end of the waveguide for transmission of ultrasonic vibrations thereto
   e) a loop formed in the wire intermediate the two legs; and
   f) loop controlling means operable from the proximal end of the sheath for enlarging the loop to grasp tissue and for closing the loop to thereby cut, and coagulate the tissue, in which the loop controlling means opens and closes the loop in the wire by moving the other leg relative to the one leg of the wire.

* * * * *